(12) United States Patent
Stalker

(10) Patent No.: US 7,918,820 B2
(45) Date of Patent: Apr. 5, 2011

(54) DEVICE FOR, AND METHOD OF, BLOCKING EMBOLI IN VESSELS SUCH AS BLOOD ARTERIES

(75) Inventor: Kent C. B. Stalker, San Marcos, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 12/557,609

(22) Filed: Sep. 11, 2009

(65) Prior Publication Data
US 2010/0004674 A1 Jan. 7, 2010

Related U.S. Application Data

(63) Continuation of application No. 09/476,689, filed on Dec. 30, 1999, now abandoned.

(51) Int. Cl.
*A61M 29/00* (2006.01)
(52) U.S. Cl. .................. 604/104; 604/107; 606/200
(58) Field of Classification Search .......... 604/104–109, 604/96.01; 606/200, 198, 127
See application file for complete search history.

(56) References Cited

U.S. PATENT DOCUMENTS

| 3,952,747 A | 4/1976 | Kimmell, Jr. |
| 4,425,908 A | 1/1984 | Simon |
| 4,494,531 A | 1/1985 | Gianturco |

(Continued)

FOREIGN PATENT DOCUMENTS
EP 0427429 A3 9/1991

(Continued)

OTHER PUBLICATIONS

Dilitation of the Carotid Artery By A Temporary Carotid Filter By A. Beck, St. Milic, A.M. Spagnoli, Nov.-Dec. Issue of OPLITAI, An International Journal on Military Medicine and Health Emergencies, pp. 67-74.

(Continued)

*Primary Examiner* — Kevin C Sirmons
*Assistant Examiner* — Phillip Gray
(74) *Attorney, Agent, or Firm* — Fulwider Patton LLP; Jonathan Feuchtwang

(57) ABSTRACT

A filtering device has a directional member and filtering member disposable in a vessel (e.g. blood artery) at a position past a lesion in the direction of fluid flow. The filtering member is made from a resilient material having properties of passing the fluid while blocking the passage of emboli in the fluid. This material may be selected from a group consisting of blood filter material and a braided/woven biocompatible material with the properties specified above. The inner end of the filtering member is attached to a shaft which provides for the disposition of the members in the vessel at the position past the lesion and the withdrawal of the members from the vessel. The directional member has a length extending at least to the vessel wall. The directional member is made from a pliable and elongatable material with properties of blocking fluid and emboli passage. The directional member is deployable within the vessel by the fluid flow in the vessel and directs the fluid in the vessel and any emboli in the fluid into the filtering member. The filtering and directional members are disposed at an acute angle relative to the shaft to create a trapping pocket. Restraining wires attached to the directional member are used to collapse the directional member and draw at least a part of the directional member into an outer sheath to prevent emboli from backflowing into the vessel.

8 Claims, 3 Drawing Sheets

U.S. PATENT DOCUMENTS

| | | |
|---|---|---|
| 4,612,931 A | 9/1986 | Dormia |
| 4,619,246 A | 10/1986 | Molgaard-Nielsen et al. |
| 4,643,184 A | 2/1987 | Mobin-Uddin |
| 4,650,466 A | 3/1987 | Luther |
| 4,662,885 A | 5/1987 | DiPisa, Jr. |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,794,928 A * | 1/1989 | Kletschka ............... 606/194 |
| 4,832,055 A | 5/1989 | Palestrant |
| 4,873,978 A | 10/1989 | Ginsburg |
| 4,921,478 A | 5/1990 | Solano et al. |
| 4,921,484 A | 5/1990 | Hillstead |
| 4,969,891 A | 11/1990 | Gewertz |
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |
| 5,064,428 A | 11/1991 | Cope et al. |
| 5,071,407 A | 12/1991 | Termin et al. |
| 5,092,839 A | 3/1992 | Kipperman |
| 5,100,423 A | 3/1992 | Fearnot |
| 5,100,425 A | 3/1992 | Fischell et al. |
| 5,102,415 A | 4/1992 | Guenther et al. |
| 5,108,419 A | 4/1992 | Reger et al. |
| 5,152,777 A | 10/1992 | Goldberg et al. |
| 5,158,548 A | 10/1992 | Lau |
| 5,160,342 A | 11/1992 | Reger et al. |
| 5,192,286 A | 3/1993 | Phan et al. |
| 5,324,304 A | 6/1994 | Rasmussen |
| 5,329,942 A | 7/1994 | Gunther et al. |
| 5,330,482 A | 7/1994 | Gibbs et al. |
| 5,350,398 A | 9/1994 | Pavcnik et al. |
| 5,370,657 A | 12/1994 | Irie |
| 5,375,612 A | 12/1994 | Cottenceau et al. |
| 5,383,887 A | 1/1995 | Nadal |
| 5,421,832 A | 6/1995 | Lefebvre |
| 5,490,859 A | 2/1996 | Mische et al. |
| 5,496,277 A | 3/1996 | Termin et al. |
| 5,496,330 A | 3/1996 | Bates et al. |
| 5,501,694 A | 3/1996 | Ressemann et al. |
| 5,549,626 A | 8/1996 | Miller et al. |
| 5,601,595 A | 2/1997 | Smith |
| 5,613,981 A | 3/1997 | Boyle et al. |
| 5,626,605 A | 5/1997 | Irie et al. |
| 5,634,942 A | 6/1997 | Chevillon et al. |
| 5,649,953 A | 7/1997 | Lefebvre |
| 5,658,296 A | 8/1997 | Bates et al. |
| 5,662,671 A | 9/1997 | Barbut et al. |
| 5,662,703 A | 9/1997 | Yurek et al. |
| 5,669,933 A | 9/1997 | Simon et al. |
| 5,681,347 A | 10/1997 | Cathcart et al. |
| 5,695,518 A | 12/1997 | Laerum |
| 5,695,519 A | 12/1997 | Summers et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,769,816 A | 6/1998 | Barbut et al. |
| 5,772,674 A | 6/1998 | Nakhjavan |
| 5,776,162 A | 7/1998 | Kleshinski |
| 5,779,716 A | 7/1998 | Cano et al. |
| 5,792,145 A | 8/1998 | Bates et al. |
| 5,792,156 A | 8/1998 | Perouse |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,650 A | 11/1998 | Imran |
| 5,836,868 A | 11/1998 | Ressemann et al. |
| 5,846,251 A | 12/1998 | Hart |
| 5,846,260 A | 12/1998 | Maas |
| 5,848,964 A | 12/1998 | Samuels |
| 5,868,708 A | 2/1999 | Hart et al. |
| 5,876,367 A | 3/1999 | Kaganov et al. |
| 5,897,567 A | 4/1999 | Ressemann et al. |
| 5,910,154 A | 6/1999 | Tsugita et al. |
| 5,911,734 A | 6/1999 | Tsugita et al. |
| 5,935,139 A | 8/1999 | Bates |
| 5,941,869 A | 8/1999 | Patterson et al. |
| 5,941,896 A | 8/1999 | Kerr |
| 5,944,728 A | 8/1999 | Bates |
| 5,954,745 A | 9/1999 | Gertler et al. |
| 5,968,071 A | 10/1999 | Chevillon et al. |
| 5,976,172 A | 11/1999 | Homsma et al. |
| 5,980,555 A | 11/1999 | Barbut et al. |
| 5,989,281 A | 11/1999 | Barbut et al. |
| 6,001,118 A | 12/1999 | Daniel et al. |
| 6,007,557 A | 12/1999 | Ambrisco et al. |
| 6,013,093 A | 1/2000 | Nott et al. |
| 6,022,336 A | 2/2000 | Zadno-Azizi et al. |
| 6,027,520 A | 2/2000 | Tsugita et al. |
| 6,042,598 A | 3/2000 | Tsugita et al. |
| 6,051,015 A | 4/2000 | Maas |
| 6,053,932 A | 4/2000 | Daniel et al. |
| 6,059,814 A | 5/2000 | Ladd |
| 6,066,158 A | 5/2000 | Engelson et al. |
| 6,074,357 A | 6/2000 | Kaganov et al. |
| 6,086,605 A | 7/2000 | Barbut et al. |
| 6,090,097 A | 7/2000 | Barbut et al. |
| 6,096,053 A | 8/2000 | Bates |
| 6,099,534 A | 8/2000 | Bates et al. |
| 6,099,549 A | 8/2000 | Bosma et al. |
| 6,117,154 A | 9/2000 | Barbut et al. |
| 6,129,739 A | 10/2000 | Khosravi |
| 6,136,015 A | 10/2000 | Kurz |
| 6,136,016 A | 10/2000 | Barbut et al. |
| 6,142,987 A | 11/2000 | Tsugita |
| 6,152,946 A | 11/2000 | Broome et al. |
| 6,152,947 A | 11/2000 | Ambrisco et al. |
| 6,165,198 A | 12/2000 | McGurk et al. |
| 6,165,200 A | 12/2000 | Tsugita et al. |
| 6,168,579 B1 | 1/2001 | Tsugita et al. |
| 6,168,604 B1 | 1/2001 | Cano |
| 6,171,327 B1 | 1/2001 | Daniel et al. |
| 6,171,328 B1 | 1/2001 | Addis |
| 6,174,318 B1 | 1/2001 | Bates et al. |
| 6,176,849 B1 | 1/2001 | Yang et al. |
| 6,179,859 B1 | 1/2001 | Bates et al. |
| 6,179,860 B1 | 1/2001 | Fulton, III et al. |
| 6,179,861 B1 | 1/2001 | Khosravi et al. |
| 6,187,025 B1 | 2/2001 | Machek |
| 6,203,561 B1 | 3/2001 | Ramee et al. |
| 6,206,868 B1 | 3/2001 | Parodi |
| 6,214,026 B1 | 4/2001 | Lepak et al. |
| 6,214,040 B1 | 4/2001 | Jayaraman |
| 6,224,620 B1 | 5/2001 | Maahs |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,746 B1 | 6/2001 | Bosma et al. |
| 6,245,012 B1 | 6/2001 | Kleshinski |
| 6,245,087 B1 | 6/2001 | Addis |
| 6,245,088 B1 | 6/2001 | Lowery |
| 6,245,089 B1 | 6/2001 | Daniel et al. |
| 6,251,119 B1 | 6/2001 | Addis |
| 6,251,122 B1 | 6/2001 | Tsukernik |
| 6,254,633 B1 | 7/2001 | Pinchuk et al. |
| 6,258,115 B1 | 7/2001 | Dubrul |
| 6,258,120 B1 | 7/2001 | McKenzie et al. |
| 6,264,663 B1 | 7/2001 | Cano |
| 6,264,672 B1 | 7/2001 | Fisher |
| 6,267,776 B1 | 7/2001 | O'Connell |
| 6,267,777 B1 | 7/2001 | Bosma et al. |
| 6,270,477 B1 | 8/2001 | Bagaoisan |
| 6,270,513 B1 | 8/2001 | Tsugita et al. |
| 6,273,901 B1 | 8/2001 | Whitcher et al. |
| 6,277,138 B1 | 8/2001 | Levinson et al. |
| 6,277,139 B1 | 8/2001 | Levinson et al. |
| 6,280,451 B1 | 8/2001 | Bates et al. |

| | | | | | | |
|---|---|---|---|---|---|---|
| 6,287,321 | B1 | 9/2001 | Jang | 6,544,276 | B1 | 4/2003 | Azizi |
| 6,290,656 | B1 | 9/2001 | Boyle et al. | 6,544,279 | B1 | 4/2003 | Hopkins et al. |
| 6,290,710 | B1 | 9/2001 | Cryer et al. | 6,544,280 | B1 | 4/2003 | Daniel et al. |
| 6,295,989 | B1 | 10/2001 | Connors, III | 6,547,759 | B1 | 4/2003 | Fisher |
| 6,306,163 | B1 | 10/2001 | Fitz | 6,551,268 | B1 | 4/2003 | Kaganov et al. |
| 6,319,242 | B1 | 11/2001 | Patterson et al. | 6,551,341 | B2 | 4/2003 | Boylan et al. |
| 6,319,268 | B1 | 11/2001 | Ambrisco et al. | 6,551,342 | B1 | 4/2003 | Shen et al. |
| 6,325,815 | B1 | 12/2001 | Kusleika et al. | 6,558,401 | B1 | 5/2003 | Azizi |
| 6,336,934 | B1 | 1/2002 | Gilson et al. | 6,558,405 | B1 | 5/2003 | McInnes |
| 6,340,364 | B2 | 1/2002 | Kanesaka | 6,562,058 | B2 | 5/2003 | Seguin |
| 6,340,465 | B1 | 1/2002 | Hsu et al. | 6,565,591 | B2 | 5/2003 | Kelly et al. |
| 6,346,116 | B1 | 2/2002 | Brooks et al. | 6,569,184 | B2 | 5/2003 | Huter |
| 6,348,056 | B1 | 2/2002 | Bates et al. | 6,575,995 | B1 | 6/2003 | Huter et al. |
| 6,355,051 | B1 | 3/2002 | Sisskind et al. | 6,575,996 | B1 | 6/2003 | Denison et al. |
| 6,361,545 | B1 | 3/2002 | Macoviak et al. | 6,575,997 | B1 | 6/2003 | Palmer et al. |
| 6,361,546 | B1 | 3/2002 | Khosravi | 6,582,447 | B1 | 6/2003 | Patel et al. |
| 6,364,895 | B1 | 4/2002 | Greenhalgh | 6,582,448 | B1 | 6/2003 | Boyle et al. |
| 6,364,896 | B1 | 4/2002 | Addis | 6,585,756 | B1 | 7/2003 | Strecker |
| 6,364,900 | B1 | 4/2002 | Heuser | 6,589,263 | B1 | 7/2003 | Hopkins et al. |
| 6,371,969 | B1 | 4/2002 | Tsugita et al. | 6,589,265 | B1 | 7/2003 | Palmer et al. |
| 6,371,970 | B1 | 4/2002 | Khosravi et al. | 6,592,546 | B1 | 7/2003 | Barbut et al. |
| 6,371,971 | B1 | 4/2002 | Tsugita et al. | 6,592,606 | B2 | 7/2003 | Huter et al. |
| 6,375,670 | B1 | 4/2002 | Greenhalgh | 6,592,607 | B1 | 7/2003 | Palmer et al. |
| 6,383,206 | B1 | 5/2002 | Gillick et al. | 6,592,616 | B1 | 7/2003 | Stack et al. |
| 6,384,062 | B1 | 5/2002 | Ikeda et al. | 6,596,011 | B2 | 7/2003 | Johnson et al. |
| 6,391,044 | B1 | 5/2002 | Yadav et al. | 6,599,307 | B1 | 7/2003 | Huter et al. |
| 6,394,978 | B1 | 5/2002 | Boyle et al. | 6,599,308 | B2 | 7/2003 | Amplatz |
| 6,395,014 | B1 | 5/2002 | Macoviak et al. | 6,602,269 | B2 | 8/2003 | Wallace et al. |
| 6,398,756 | B2 | 6/2002 | Peterson et al. | 6,602,271 | B2 | 8/2003 | Adams et al. |
| 6,402,771 | B1 | 6/2002 | Palmer et al. | 6,602,272 | B2 | 8/2003 | Boylan et al. |
| 6,406,471 | B1 | 6/2002 | Jang et al. | 6,602,273 | B2 | 8/2003 | Marshall |
| 6,423,032 | B2 | 7/2002 | Parodi | 6,605,102 | B1 | 8/2003 | Mazzocchi et al. |
| 6,423,086 | B1 | 7/2002 | Barbut et al. | 6,605,111 | B2 | 8/2003 | Bose et al. |
| 6,425,909 | B1 | 7/2002 | Dieck et al. | 6,607,506 | B2 | 8/2003 | Kletschka |
| 6,428,559 | B1 | 8/2002 | Johnson | 6,610,077 | B1 | 8/2003 | Hancock et al. |
| 6,432,122 | B1 | 8/2002 | Gilson et al. | 6,616,679 | B1 | 9/2003 | Khosravi et al. |
| 6,436,121 | B1 | 8/2002 | Blom | 6,616,680 | B1 | 9/2003 | Thielen |
| 6,443,926 | B1 | 9/2002 | Kletschka | 6,616,681 | B2 | 9/2003 | Hanson et al. |
| 6,443,971 | B1 | 9/2002 | Boylan et al. | 6,616,682 | B2 | 9/2003 | Joergensen et al. |
| 6,443,972 | B1 | 9/2002 | Bosma | 6,620,148 | B1 | 9/2003 | Tsugita et al. |
| 6,443,979 | B1 | 9/2002 | Stalker et al. | 6,620,182 | B1 | 9/2003 | Khosravi |
| 6,447,530 | B1 | 9/2002 | Ostrovsky et al. | 6,623,450 | B1 | 9/2003 | Dutta |
| 6,447,531 | B1 | 9/2002 | Amplatz | 6,629,953 | B1 | 10/2003 | Boyd |
| 6,450,989 | B2 | 9/2002 | Dubrul et al. | 6,632,236 | B2 | 10/2003 | Hogendijk |
| 6,458,139 | B1 | 10/2002 | Palmer et al. | 6,632,241 | B1 | 10/2003 | Hancock et al. |
| 6,461,370 | B1 | 10/2002 | Gray et al. | 6,635,068 | B1 | 10/2003 | Dubrul et al. |
| 6,468,291 | B2 | 10/2002 | Bates et al. | 6,635,070 | B2 | 10/2003 | Leeflang et al. |
| 6,482,222 | B1 | 11/2002 | Bruckheimer et al. | 6,638,293 | B1 | 10/2003 | Makower et al. |
| 6,485,456 | B1 | 11/2002 | Kletschka | 6,638,294 | B1 | 10/2003 | Palmer |
| 6,485,497 | B2 | 11/2002 | Wensel et al. | 6,645,220 | B1 | 11/2003 | Huter et al. |
| 6,485,500 | B1 | 11/2002 | Kokish et al. | 6,645,221 | B1 | 11/2003 | Richter |
| 6,485,501 | B1 | 11/2002 | Green | 6,645,223 | B2 | 11/2003 | Boyle et al. |
| 6,485,502 | B2 | 11/2002 | Don Michael et al. | 6,645,224 | B2 | 11/2003 | Gilson et al. |
| 6,485,507 | B1 | 11/2002 | Walak et al. | 6,652,480 | B1 | 11/2003 | Imran et al. |
| 6,494,895 | B2 | 12/2002 | Addis | 6,652,505 | B1 | 11/2003 | Tsugita et al. |
| 6,499,487 | B1 | 12/2002 | McKenzie et al. | 6,652,554 | B1 | 11/2003 | Wholey et al. |
| 6,500,166 | B1 | 12/2002 | Zadno Azizi et al. | 6,652,557 | B1 | 11/2003 | MacDonald |
| 6,506,203 | B1 | 1/2003 | Boyle et al. | 6,656,202 | B2 | 12/2003 | Papp et al. |
| 6,506,205 | B2 | 1/2003 | Goldberg et al. | 6,656,203 | B2 | 12/2003 | Roth et al. |
| 6,511,492 | B1 | 1/2003 | Rosenbluth | 6,656,204 | B2 | 12/2003 | Ambrisco et al. |
| 6,511,496 | B1 | 1/2003 | Huter et al. | 6,656,351 | B2 | 12/2003 | Boyle |
| 6,511,497 | B1 | 1/2003 | Braun et al. | 6,660,021 | B1 | 12/2003 | Palmer et al. |
| 6,511,503 | B1 | 1/2003 | Burkett et al. | 6,663,650 | B2 | 12/2003 | Sepetka et al. |
| 6,514,273 | B1 | 2/2003 | Voss et al. | 6,663,651 | B2 | 12/2003 | Krolik et al. |
| 6,517,550 | B1 | 2/2003 | Konya et al. | 6,663,652 | B2 | 12/2003 | Daniel et al. |
| 6,517,559 | B1 | 2/2003 | O'Connell | 6,673,090 | B2 | 1/2004 | Root et al. |
| 6,520,978 | B1 | 2/2003 | Blackledge et al. | 6,676,666 | B2 | 1/2004 | Vrba et al. |
| 6,527,746 | B1 | 3/2003 | Oslund et al. | 6,676,682 | B1 | 1/2004 | Tsugita et al. |
| 6,527,791 | B2 | 3/2003 | Fisher | 6,676,683 | B1 | 1/2004 | Addis |
| 6,530,939 | B1 | 3/2003 | Hopkins et al. | 6,679,902 | B1 | 1/2004 | Boyle et al. |
| 6,530,940 | B2 | 3/2003 | Fisher | 6,679,903 | B2 | 1/2004 | Kurz |
| 6,533,800 | B1 | 3/2003 | Barbut | 6,682,546 | B2 | 1/2004 | Amplatz |
| 6,537,294 | B1 | 3/2003 | Boyle et al. | 6,685,722 | B1 | 2/2004 | Rosenbluth et al. |
| 6,537,295 | B2 | 3/2003 | Peterson | 6,689,151 | B2 | 2/2004 | Becker et al. |
| 6,537,296 | B2 | 3/2003 | Levinson et al. | 6,692,513 | B2 | 2/2004 | Streeter et al. |
| 6,537,297 | B2 | 3/2003 | Tsugita et al. | 6,695,813 | B1 | 2/2004 | Boyle et al. |
| 6,540,722 | B1 | 4/2003 | Boyle et al. | 6,695,858 | B1 | 2/2004 | Dubrul et al. |
| 6,540,767 | B1 | 4/2003 | Walak et al. | 6,695,864 | B2 | 2/2004 | Macoviak et al. |
| 6,540,768 | B1 | 4/2003 | Diaz et al. | 6,696,666 | B2 | 2/2004 | Merdan et al. |

| | | | | | | |
|---|---|---|---|---|---|---|
| 6,699,260 B2 | 3/2004 | Dubrul et al. | | 6,989,021 B2 | 1/2006 | Bosma et al. |
| 6,702,834 B1 | 3/2004 | Yassour et al. | | 6,989,027 B2 | 1/2006 | Allen et al. |
| 6,706,055 B2 | 3/2004 | Douk et al. | | 6,991,641 B2 | 1/2006 | Diaz et al. |
| 6,712,834 B2 | 3/2004 | Boyle et al. | | 6,991,642 B2 | 1/2006 | Peterson |
| 6,712,835 B2 | 3/2004 | Mazzocchi et al. | | RE38,972 E | 2/2006 | Purdy |
| 6,716,231 B1 | 4/2004 | Rafiee et al. | | 6,994,718 B2 | 2/2006 | Groothuis et al. |
| 6,723,085 B2 | 4/2004 | Jang et al. | | 6,997,938 B2 | 2/2006 | Wang et al. |
| 6,726,701 B2 | 4/2004 | Gilson | | 6,997,939 B2 | 2/2006 | Linder et al. |
| 6,726,702 B2 | 4/2004 | Khosravi | | 7,001,406 B2 | 2/2006 | Eskuri et al. |
| 6,726,703 B2 | 4/2004 | Broome et al. | | 7,001,407 B2 | 2/2006 | Hansen et al. |
| 6,740,061 B1 | 5/2004 | Oslund et al. | | 7,004,954 B1 | 2/2006 | Voss et al. |
| 6,743,247 B1 | 6/2004 | Levinson et al. | | 7,004,955 B2 | 2/2006 | Shen et al. |
| 6,746,469 B2 | 6/2004 | Mouw | | 7,004,956 B2 | 2/2006 | Palmer et al. |
| 6,752,819 B1 | 6/2004 | Brady et al. | | 7,004,964 B2 | 2/2006 | Thompson et al. |
| 6,755,846 B1 | 6/2004 | Yadav | | 7,011,671 B2 | 3/2006 | Welch |
| 6,758,855 B2 | 7/2004 | Fulton, III et al. | | 7,011,672 B2 | 3/2006 | Barbut et al. |
| 6,761,727 B1 | 7/2004 | Ladd | | 7,014,647 B2 | 3/2006 | Brady et al. |
| 6,773,448 B2 | 8/2004 | Kusleika et al. | | 7,018,372 B2 | 3/2006 | Casey |
| 6,790,219 B1 | 9/2004 | Murphy | | 7,018,385 B2 | 3/2006 | Bates et al. |
| 6,793,666 B2 | 9/2004 | Hansen et al. | | 7,018,393 B1 | 3/2006 | Boyle et al. |
| 6,793,668 B1 | 9/2004 | Fisher | | 7,029,440 B2 | 4/2006 | Broome et al. |
| 6,800,080 B1 | 10/2004 | Bates | | 7,033,375 B2 | 4/2006 | Mazocchi et al. |
| 6,814,739 B2 | 11/2004 | Secrest et al. | | 7,037,320 B2 | 5/2006 | Brady et al. |
| 6,818,006 B2 | 11/2004 | Douk et al. | | 7,041,116 B2 | 5/2006 | Goto et al. |
| 6,837,898 B2 | 1/2005 | Boyle | | 7,044,958 B2 | 5/2006 | Douk et al. |
| 6,840,950 B2 | 1/2005 | Stanford et al. | | 7,048,752 B2 | 5/2006 | Mazzocchi |
| 6,843,798 B2 | 1/2005 | Kusleika et al. | | 7,048,758 B2 | 5/2006 | Boyle et al. |
| 6,846,316 B2 | 1/2005 | Abrams | | 7,056,328 B2 | 6/2006 | Arnott |
| 6,846,317 B1 | 1/2005 | Nigon | | 7,060,082 B2 | 6/2006 | Goll et al. |
| 6,863,696 B2 | 3/2005 | Kantsevitcha et al. | | 7,077,854 B2 | 7/2006 | Khosravi |
| 6,866,677 B2 | 3/2005 | Douk et al. | | 7,094,243 B2 | 8/2006 | Mulholland |
| 6,872,216 B2 | 3/2005 | Daniel et al. | | 7,094,249 B1 | 8/2006 | Broome et al. |
| 6,878,151 B2 | 4/2005 | Carrison et al. | | 7,097,440 B2 | 8/2006 | Papp et al. |
| 6,878,153 B2 | 4/2005 | Linder et al. | | 7,097,651 B2 | 8/2006 | Harrison et al. |
| 6,887,256 B2 | 5/2005 | Gilson et al. | | 7,101,379 B2 | 9/2006 | Gregory, Jr et al. |
| 6,887,257 B2 | 5/2005 | Salaheih et al. | | 7,101,380 B2 | 9/2006 | Khachin et al. |
| 6,887,258 B2 | 5/2005 | Denison | | 7,108,707 B2 | 9/2006 | Huter et al. |
| 6,888,098 B1 | 5/2005 | Merdan et al. | | 2002/0091408 A1 | 7/2002 | Sutton et al. |
| 6,890,340 B2 | 5/2005 | Duane | | 2002/0091409 A1 | 7/2002 | Sutton et al. |
| 6,890,341 B2 | 5/2005 | Dieck et al. | | 2002/0095141 A1 | 7/2002 | Belef et al. |
| 6,893,450 B2 | 5/2005 | Foster | | 2002/0099407 A1 | 7/2002 | Becker et al. |
| 6,893,451 B2 | 5/2005 | Cano et al. | | 2002/0103501 A1 | 8/2002 | Diaz et al. |
| 6,896,690 B1 | 5/2005 | Lambrecht et al. | | 2002/0107541 A1 | 8/2002 | Vale et al. |
| 6,896,691 B2 | 5/2005 | Boylan | | 2002/0111648 A1 | 8/2002 | Kusleika et al. |
| 6,902,540 B2 | 6/2005 | Dorros et al. | | 2002/0111649 A1 | 8/2002 | Russo et al. |
| 6,908,474 B2 | 6/2005 | Hogenkijk et al. | | 2002/0115942 A1 | 8/2002 | Stanford et al. |
| 6,911,036 B2 | 6/2005 | Douk et al. | | 2002/0120286 A1 | 8/2002 | DoBrava et al. |
| 6,913,612 B2 | 7/2005 | Palmer et al. | | 2002/0120287 A1 | 8/2002 | Huter |
| 6,918,921 B2 | 7/2005 | Brady et al. | | 2002/0121472 A1 | 9/2002 | Garner et al. |
| 6,929,652 B1 | 8/2005 | Andrews | | 2002/0123720 A1 | 9/2002 | Kusleika et al. |
| 6,932,830 B2 | 8/2005 | Ungs | | 2002/0123755 A1 | 9/2002 | Lowe et al. |
| 6,932,831 B2 | 8/2005 | Forber | | 2002/0128679 A1 | 9/2002 | Turovskiy et al. |
| 6,936,058 B2 | 8/2005 | Forde et al. | | 2002/0128680 A1 | 9/2002 | Pavlovic |
| 6,936,059 B2 | 8/2005 | Belef | | 2002/0128681 A1 | 9/2002 | Broome et al. |
| 6,939,361 B1 | 9/2005 | Kleshinski | | 2002/0133092 A1 | 9/2002 | Oslund et al. |
| 6,939,362 B2 | 9/2005 | Boyle et al. | | 2002/0138094 A1 | 9/2002 | Borillo et al. |
| 6,942,673 B2 | 9/2005 | Bates et al. | | 2002/0138095 A1 | 9/2002 | Mazzocchi et al. |
| 6,949,103 B2 | 9/2005 | Mazzocchi et al. | | 2002/0143360 A1 | 10/2002 | Douk et al. |
| 6,951,570 B2 | 10/2005 | Linder et al. | | 2002/0143361 A1 | 10/2002 | Douk et al. |
| 6,953,471 B1 | 10/2005 | Lilly et al. | | 2002/0151927 A1 | 10/2002 | Douk et al. |
| 6,953,472 B2 | 10/2005 | Palmer et al. | | 2002/0156456 A1 | 10/2002 | Fisher |
| 6,958,074 B2 | 10/2005 | Russell | | 2002/0156457 A1 | 10/2002 | Fisher |
| 6,960,370 B2 | 11/2005 | Monni et al. | | 2002/0161390 A1 | 10/2002 | Mouw |
| 6,962,598 B2 | 11/2005 | Linder et al. | | 2002/0161392 A1 | 10/2002 | Dubrul |
| 6,964,670 B1 | 11/2005 | Shah | | 2002/0161393 A1 | 10/2002 | Demond et al. |
| 6,964,672 B2 | 11/2005 | Brady | | 2002/0161395 A1 | 10/2002 | Douk et al. |
| 6,964,673 B2 | 11/2005 | Tsugita et al. | | 2002/0165576 A1 | 11/2002 | Boyle et al. |
| 6,969,395 B2 | 11/2005 | Eskuri | | 2002/0169414 A1 | 11/2002 | Kletschka |
| 6,969,396 B2 | 11/2005 | Krolik et al. | | 2002/0169458 A1 | 11/2002 | Connors, III |
| 6,969,402 B2 | 11/2005 | Bales et al. | | 2002/0169472 A1 | 11/2002 | Douk et al. |
| 6,970,730 B2 | 11/2005 | Fuimaono et al. | | 2002/0169474 A1 | 11/2002 | Kusleika et al. |
| 6,972,025 B2 | 12/2005 | WasDyke | | 2002/0173815 A1 | 11/2002 | Hogendijk et al. |
| 6,973,340 B2 | 12/2005 | Fuimaono et al. | | 2002/0173817 A1 | 11/2002 | Kletschka et al. |
| 6,974,468 B2 | 12/2005 | DoBrava et al. | | 2002/0188313 A1 | 12/2002 | Johnson et al. |
| 6,974,469 B2 | 12/2005 | Broome et al. | | 2002/0188314 A1 | 12/2002 | Anderson et al. |
| 6,979,343 B2 | 12/2005 | Russo et al. | | 2002/0193825 A1 | 12/2002 | McGuckin et al. |
| 6,979,344 B2 | 12/2005 | Jones et al. | | 2002/0193826 A1 | 12/2002 | McGuckin et al. |
| 6,986,778 B2 | 1/2006 | Zadno-Azizi | | 2002/0193827 A1 | 12/2002 | McGuckin et al. |
| 6,989,019 B2 | 1/2006 | Mazzocchi et al. | | 2002/0193828 A1 | 12/2002 | Griffin et al. |

| | | |
|---|---|---|
| 2003/0004536 A1 | 1/2003 | Boylan et al. |
| 2003/0004537 A1 | 1/2003 | Boyle et al. |
| 2003/0004539 A1 | 1/2003 | Linder et al. |
| 2003/0004540 A1 | 1/2003 | Linder et al. |
| 2003/0004541 A1 | 1/2003 | Linder et al. |
| 2003/0009188 A1 | 1/2003 | Linder et al. |
| 2003/0009189 A1 | 1/2003 | Gilson et al. |
| 2003/0015206 A1 | 1/2003 | Roth et al. |
| 2003/0018354 A1 | 1/2003 | Roth et al. |
| 2003/0023265 A1 | 1/2003 | Forber |
| 2003/0028238 A1 | 2/2003 | Burkett et al. |
| 2003/0032941 A1 | 2/2003 | Boyle et al. |
| 2003/0032977 A1 | 2/2003 | Brady et al. |
| 2003/0040772 A1 | 2/2003 | Hyodoh et al. |
| 2003/0042186 A1 | 3/2003 | Boyle et al. |
| 2003/0045898 A1 | 3/2003 | Harrison et al. |
| 2003/0057156 A1 | 3/2003 | Peterson et al. |
| 2003/0060782 A1 | 3/2003 | Bose et al. |
| 2003/0060843 A1 | 3/2003 | Boucher |
| 2003/0060844 A1 | 3/2003 | Borillo et al. |
| 2003/0065354 A1 | 4/2003 | Boyle et al. |
| 2003/0069596 A1 | 4/2003 | Eskuri |
| 2003/0069597 A1 | 4/2003 | Petersen |
| 2003/0078519 A1 | 4/2003 | Salahieh et al. |
| 2003/0078614 A1 | 4/2003 | Salahieh et al. |
| 2003/0083692 A1 | 5/2003 | Vrba et al. |
| 2003/0083693 A1 | 5/2003 | Daniel et al. |
| 2003/0097095 A1 | 5/2003 | Brady et al. |
| 2003/0100917 A1 | 5/2003 | Boyle et al. |
| 2003/0100918 A1 | 5/2003 | Duane |
| 2003/0105484 A1 | 6/2003 | Boyle et al. |
| 2003/0109824 A1 | 6/2003 | Anderson et al. |
| 2003/0114879 A1 | 6/2003 | Euteneuer et al. |
| 2003/0114880 A1 | 6/2003 | Hansen et al. |
| 2003/0120303 A1 | 6/2003 | Boyle et al. |
| 2003/0125764 A1 | 7/2003 | Brady et al. |
| 2003/0130680 A1 | 7/2003 | Russell |
| 2003/0130681 A1 | 7/2003 | Ungs |
| 2003/0130682 A1 | 7/2003 | Broome et al. |
| 2003/0130684 A1 | 7/2003 | Brady et al. |
| 2003/0130685 A1 | 7/2003 | Daniel et al. |
| 2003/0130686 A1 | 7/2003 | Daniel et al. |
| 2003/0130687 A1 | 7/2003 | Daniel et al. |
| 2003/0130688 A1 | 7/2003 | Daniel et al. |
| 2003/0135162 A1 | 7/2003 | Deyette, Jr. et al. |
| 2003/0135232 A1 | 7/2003 | Douk et al. |
| 2003/0139764 A1 | 7/2003 | Levinson et al. |
| 2003/0144685 A1 | 7/2003 | Boyle et al. |
| 2003/0144689 A1 | 7/2003 | Brady et al. |
| 2003/0150821 A1 | 8/2003 | Bates et al. |
| 2003/0153935 A1 | 8/2003 | Mialhe |
| 2003/0153942 A1 | 8/2003 | Wang et al. |
| 2003/0153943 A1 | 8/2003 | Michael et al. |
| 2003/0158574 A1 | 8/2003 | Esch et al. |
| 2003/0163064 A1 | 8/2003 | Vrba et al. |
| 2003/0171770 A1 | 9/2003 | Kusleika et al. |
| 2003/0171771 A1 | 9/2003 | Anderson et al. |
| 2003/0171803 A1 | 9/2003 | Shimon |
| 2003/0176884 A1 | 9/2003 | Berrada et al. |
| 2003/0176885 A1 | 9/2003 | Broome et al. |
| 2003/0176886 A1 | 9/2003 | Wholey et al. |
| 2003/0176889 A1 | 9/2003 | Boyle et al. |
| 2003/0181942 A1 | 9/2003 | Sutton et al. |
| 2003/0181943 A1 | 9/2003 | Daniel et al. |
| 2003/0187474 A1 | 10/2003 | Keegan et al. |
| 2003/0187475 A1 | 10/2003 | Tsugita et al. |
| 2003/0187495 A1 | 10/2003 | Cully et al. |
| 2003/0191493 A1 | 10/2003 | Epstein et al. |
| 2003/0195554 A1 | 10/2003 | Shen et al. |
| 2003/0195555 A1 | 10/2003 | Khairkhahan et al. |
| 2003/0195556 A1 | 10/2003 | Stack et al. |
| 2003/0199819 A1 | 10/2003 | Beck |
| 2003/0199921 A1 | 10/2003 | Palmer et al. |
| 2003/0204168 A1 | 10/2003 | Bosme et al. |
| 2003/0204202 A1 | 10/2003 | Palmer et al. |
| 2003/0208222 A1 | 11/2003 | Zadno-Azizi |
| 2003/0208224 A1 | 11/2003 | Broome |
| 2003/0208225 A1 | 11/2003 | Goll et al. |
| 2003/0208226 A1 | 11/2003 | Bruckheimer et al. |
| 2003/0208227 A1 | 11/2003 | Thomas |
| 2003/0208228 A1 | 11/2003 | Gilson et al. |
| 2003/0208229 A1 | 11/2003 | Kletschka |
| 2003/0212361 A1 | 11/2003 | Boyle et al. |
| 2003/0212429 A1 | 11/2003 | Keegan et al. |
| 2003/0212431 A1 | 11/2003 | Brady et al. |
| 2003/0212434 A1 | 11/2003 | Thielen |
| 2003/0216774 A1 | 11/2003 | Larson |
| 2003/0220665 A1 | 11/2003 | Eskuri et al. |
| 2003/0225418 A1 | 12/2003 | Eskuri et al. |
| 2003/0225435 A1 | 12/2003 | Huter et al. |
| 2003/0229295 A1 | 12/2003 | Houde et al. |
| 2003/0229374 A1 | 12/2003 | Brady et al. |
| 2003/0233117 A1 | 12/2003 | Adams et al. |
| 2003/0236545 A1 | 12/2003 | Gilson |
| 2004/0002730 A1 | 1/2004 | Denison et al. |
| 2004/0006361 A1 | 1/2004 | Boyle et al. |
| 2004/0006364 A1 | 1/2004 | Ladd |
| 2004/0006365 A1 | 1/2004 | Brady et al. |
| 2004/0006366 A1 | 1/2004 | Huter et al. |
| 2004/0006367 A1 | 1/2004 | Johnson et al. |
| 2004/0006368 A1 | 1/2004 | Mazzocchi et al. |
| 2004/0015184 A1 | 1/2004 | Boyle et al. |
| 2004/0019363 A1 | 1/2004 | Hanson et al. |
| 2004/0034385 A1 | 2/2004 | Gilson et al. |
| 2004/0039411 A1 | 2/2004 | Gilson et al. |
| 2004/0044359 A1 | 3/2004 | Renati et al. |
| 2004/0044360 A1 | 3/2004 | Lowe |
| 2004/0049226 A1 | 3/2004 | Keegan et al. |
| 2004/0059372 A1 | 3/2004 | Tsugita |
| 2004/0059373 A1 | 3/2004 | Shapiro et al. |
| 2004/0082697 A1 | 4/2004 | Broome et al. |
| 2004/0082968 A1 | 4/2004 | Krolik et al. |
| 2004/0088000 A1 | 5/2004 | Muller |
| 2004/0088002 A1 | 5/2004 | Boyle et al. |
| 2004/0093009 A1 | 5/2004 | Denison et al. |
| 2004/0093010 A1 | 5/2004 | Gesswein et al. |
| 2004/0093011 A1 | 5/2004 | Vrba |
| 2004/0093012 A1 | 5/2004 | Cully et al. |
| 2004/0093013 A1 | 5/2004 | Brady et al. |
| 2004/0098022 A1 | 5/2004 | Barone |
| 2004/0098026 A1 | 5/2004 | Joergensen et al. |
| 2004/0098032 A1 | 5/2004 | Papp et al. |
| 2004/0098033 A1 | 5/2004 | Leeflang et al. |
| 2004/0102807 A1 | 5/2004 | Kusleika et al. |
| 2004/0106944 A1 | 6/2004 | Daniel et al. |
| 2004/0111111 A1 | 6/2004 | Lin |
| 2004/0116960 A1 | 6/2004 | Demond et al. |
| 2004/0122466 A1 | 6/2004 | Bales |
| 2004/0127933 A1 | 7/2004 | Demond et al. |
| 2004/0127934 A1 | 7/2004 | Gilson et al. |
| 2004/0127936 A1 | 7/2004 | Salaheih et al. |
| 2004/0138693 A1 | 7/2004 | Eskuri et al. |
| 2004/0138694 A1 | 7/2004 | Tran et al. |
| 2004/0138696 A1 | 7/2004 | Drasler et al. |
| 2004/0147955 A1 | 7/2004 | Beulke et al. |
| 2004/0153118 A1 | 8/2004 | Clubb et al. |
| 2004/0153119 A1 | 8/2004 | Kusleika et al. |
| 2004/0158275 A1 | 8/2004 | Crank et al. |
| 2004/0158277 A1 | 8/2004 | Lowe et al. |
| 2004/0158278 A1 | 8/2004 | Becker et al. |
| 2004/0158279 A1 | 8/2004 | Petersen |
| 2004/0158280 A1 | 8/2004 | Morris et al. |
| 2004/0158281 A1 | 8/2004 | Boylan et al. |
| 2004/0167564 A1 | 8/2004 | Fedie |
| 2004/0167565 A1 | 8/2004 | Beulke et al. |
| 2004/0167566 A1 | 8/2004 | Beulke et al. |
| 2004/0167567 A1 | 8/2004 | Cano et al. |
| 2004/0167568 A1 | 8/2004 | Boyle et al. |
| 2004/0172055 A1 | 9/2004 | Huter et al. |
| 2004/0176794 A1 | 9/2004 | Khosravi |
| 2004/0193208 A1 | 9/2004 | Talpade et al. |
| 2004/0199198 A1 | 10/2004 | Beulke et al. |
| 2004/0199199 A1 | 10/2004 | Krolik et al. |
| 2004/0199203 A1 | 10/2004 | Oslund et al. |
| 2004/0204737 A1 | 10/2004 | Boismier et al. |
| 2004/0210250 A1 | 10/2004 | Eskuri |
| 2004/0220608 A1 | 11/2004 | D'Aquanni et al. |
| 2004/0220609 A1 | 11/2004 | Douk et al. |

| Publication No. | Date | Inventor |
|---|---|---|
| 2004/0220611 A1 | 11/2004 | Ogle |
| 2004/0225322 A1 | 11/2004 | Garrison et al. |
| 2004/0236368 A1 | 11/2004 | McGuckin, Jr. et al. |
| 2004/0236369 A1 | 11/2004 | Dubrul |
| 2004/0249409 A1 | 12/2004 | Krolik et al. |
| 2004/0254601 A1 | 12/2004 | Eskuri |
| 2004/0254602 A1 | 12/2004 | Lehe et al. |
| 2004/0260308 A1 | 12/2004 | Gilson et al. |
| 2004/0260333 A1 | 12/2004 | Dubrul et al. |
| 2004/0267301 A1 | 12/2004 | Boylan et al. |
| 2004/0267302 A1 | 12/2004 | Gilson et al. |
| 2005/0004594 A1 | 1/2005 | Nool et al. |
| 2005/0004595 A1 | 1/2005 | Boyle et al. |
| 2005/0004597 A1 | 1/2005 | McGuckin, Jr. et al. |
| 2005/0010245 A1 | 1/2005 | Wasicek |
| 2005/0010246 A1 | 1/2005 | Streeter et al. |
| 2005/0010247 A1 | 1/2005 | Kusleika et al. |
| 2005/0021075 A1 | 1/2005 | Bonnette et al. |
| 2005/0021076 A1 | 1/2005 | Mazzocchi et al. |
| 2005/0055048 A1 | 3/2005 | Dieck et al. |
| 2005/0070953 A1 | 3/2005 | Riley |
| 2005/0075663 A1 | 4/2005 | Boyle et al. |
| 2005/0080446 A1 | 4/2005 | Gilson et al. |
| 2005/0085842 A1 | 4/2005 | Eversull et al. |
| 2005/0090845 A1 | 4/2005 | Boyd |
| 2005/0090857 A1 | 4/2005 | Kusleika et al. |
| 2005/0090858 A1 | 4/2005 | Pavlovic |
| 2005/0096691 A1 | 5/2005 | Groothuis et al. |
| 2005/0096692 A1 | 5/2005 | Linder et al. |
| 2005/0101986 A1 | 5/2005 | Daniel et al. |
| 2005/0101987 A1 | 5/2005 | Salahich |
| 2005/0101988 A1 | 5/2005 | Stanford et al. |
| 2005/0101989 A1 | 5/2005 | Cully et al. |
| 2005/0113865 A1 | 5/2005 | Daniel et al. |
| 2005/0119688 A1 | 6/2005 | Bergheim |
| 2005/0119689 A1 | 6/2005 | Mazzocchi et al. |
| 2005/0119690 A1 | 6/2005 | Mazzocchi et al. |
| 2005/0119691 A1 | 6/2005 | Daniel et al. |
| 2005/0124931 A1 | 6/2005 | Fulton et al. |
| 2005/0125023 A1 | 6/2005 | Bates et al. |
| 2005/0131450 A1 | 6/2005 | Nicholson et al. |
| 2005/0131453 A1 | 6/2005 | Parodi |
| 2005/0149110 A1 | 7/2005 | Wholey et al. |
| 2005/0149112 A1 | 7/2005 | Barbut |
| 2005/0149113 A1 | 7/2005 | Douk et al. |
| 2005/0159772 A1 | 7/2005 | Lowe et al. |
| 2005/0159773 A1 | 7/2005 | Broome et al. |
| 2005/0159774 A1 | 7/2005 | Belef |
| 2005/0171573 A1 | 8/2005 | Salahieh et al. |
| 2005/0177187 A1 | 8/2005 | Gray et al. |
| 2005/0182440 A1 | 8/2005 | Bates et al. |
| 2005/0182441 A1 | 8/2005 | Denison et al. |
| 2005/0192623 A1 | 9/2005 | Mazzocchi et al. |
| 2005/0192624 A1 | 9/2005 | Mazzocchi et al. |
| 2005/0203567 A1 | 9/2005 | Linder et al. |
| 2005/0203569 A1 | 9/2005 | Kusleika et al. |
| 2005/0203570 A1 | 9/2005 | Mazzocchi et al. |
| 2005/0203571 A1 | 9/2005 | Mazzocchi et al. |
| 2005/0209634 A1 | 9/2005 | Brady et al. |
| 2005/0209635 A1 | 9/2005 | Gilson et al. |
| 2005/0216051 A1 | 9/2005 | Mazzocchi et al. |
| 2005/0216052 A1 | 9/2005 | Mazzocchi et al. |
| 2005/0216053 A1 | 9/2005 | Douk et al. |
| 2005/0303568 | 9/2005 | Burg et al. |
| 2005/0222583 A1 | 10/2005 | Cano et al. |
| 2005/0222604 A1 | 10/2005 | Schaeffer et al. |
| 2005/0222607 A1 | 10/2005 | Palmer et al. |
| 2005/0228437 A1 | 10/2005 | Gilson et al. |
| 2005/0228438 A1 | 10/2005 | Sachar et al. |
| 2005/0228439 A1 | 10/2005 | Andrews et al. |
| 2005/0234502 A1 | 10/2005 | Gilson et al. |
| 2005/0240215 A1 | 10/2005 | Ellis |
| 2005/0245866 A1 | 11/2005 | Azizi |
| 2005/0267517 A1 | 12/2005 | Ungs |
| 2005/0283184 A1 | 12/2005 | Gilson et al. |
| 2005/0283185 A1 | 12/2005 | Linder et al. |
| 2005/0283186 A1 | 12/2005 | Berrada et al. |
| 2005/0288705 A1 | 12/2005 | Gilson et al. |
| 2006/0004403 A1 | 1/2006 | Gilson et al. |
| 2006/0004405 A1 | 1/2006 | Salaheih et al. |
| 2006/0015138 A1 | 1/2006 | Gertner et al. |
| 2006/0015139 A1 | 1/2006 | Tsugita et al. |
| 2006/0015141 A1 | 1/2006 | Linder et al. |
| 2006/0020285 A1 | 1/2006 | Niermann |
| 2006/0020286 A1 | 1/2006 | Niermann |
| 2006/0025803 A1 | 2/2006 | Mitelberg et al. |
| 2006/0025804 A1 | 2/2006 | Krolik et al. |
| 2006/0025805 A1 | 2/2006 | DoBrava et al. |
| 2006/0030876 A1 | 2/2006 | Peacock, II et al. |
| 2006/0030877 A1 | 2/2006 | Martinez et al. |
| 2006/0030878 A1 | 2/2006 | Anderson et al. |
| 2006/0052817 A1 | 3/2006 | Russo et al. |
| 2006/0074446 A1 | 4/2006 | Gilson et al. |
| 2006/0095069 A1 | 5/2006 | Shah et al. |
| 2006/0100659 A1 | 5/2006 | Dinh et al. |
| 2006/0100662 A1 | 5/2006 | Daniel et al. |
| 2006/0100663 A1 | 5/2006 | Palmer et al. |
| 2006/0116715 A1 | 6/2006 | Khosravi et al. |
| 2006/0122643 A1 | 6/2006 | Wasicek |
| 2006/0122644 A1 | 6/2006 | Brady et al. |
| 2006/0122645 A1 | 6/2006 | Brady et al. |
| 2006/0129181 A1 | 6/2006 | Callol et al. |
| 2006/0129182 A1 | 6/2006 | Gilson et al. |
| 2006/0129183 A1 | 6/2006 | Boyle et al. |
| 2006/0149312 A1 | 7/2006 | Arguello et al. |
| 2006/0149313 A1 | 7/2006 | Arguello et al. |
| 2006/0149314 A1 | 7/2006 | Borillo et al. |
| 2006/0155322 A1 | 7/2006 | Sater et al. |
| 2006/0161198 A1 | 7/2006 | Sakai et al. |
| 2006/0167491 A1 | 7/2006 | Wholey et al. |
| 2006/0184194 A1 | 8/2006 | Pal et al. |
| 2006/0190025 A1 | 8/2006 | Lehe et al. |
| 2006/0195137 A1 | 8/2006 | Sepetka et al. |
| 2006/0195138 A1 | 8/2006 | Goll et al. |
| 2006/0200047 A1 | 9/2006 | Galdonik et al. |
| 2006/0200191 A1 | 9/2006 | Zadno-Azizi |
| 2006/0206139 A1 | 9/2006 | Tekulve |

FOREIGN PATENT DOCUMENTS

| | | |
|---|---|---|
| EP | 0472334 A1 | 2/1992 |
| EP | 0533511 A1 | 3/1993 |
| EP | 1 127 556 A2 | 8/2001 |
| EP | 1 127 556 A3 | 8/2001 |
| FR | 2580504 A1 | 10/1986 |
| GB | 2020557 | 11/1979 |
| WO | WO92/03097 | 3/1992 |
| WO | WO96/01591 | 1/1996 |
| WO | WO97/17100 | 5/1997 |
| WO | WO98/02084 | 1/1998 |
| WO | WO98/33443 | 8/1998 |
| WO | WO99/16382 | 4/1999 |
| WO | WO99/22673 | 5/1999 |
| WO | WO99/23976 | 5/1999 |
| WO | WO99/44510 | 9/1999 |
| WO | WO00/67667 | 11/2000 |
| WO | WO01/10346 | 2/2001 |
| WO | WO01/12082 | 2/2001 |
| WO | WO01/45592 | 6/2001 |
| WO | WO01/87183 | 11/2001 |
| WO | WO02/28292 | 4/2002 |
| WO | WO2004/021928 | 3/2004 |

OTHER PUBLICATIONS

Minibasket for Percutaneous Embolectomy and Filter Protection Against Distal Embolization: Technical Note.

* cited by examiner

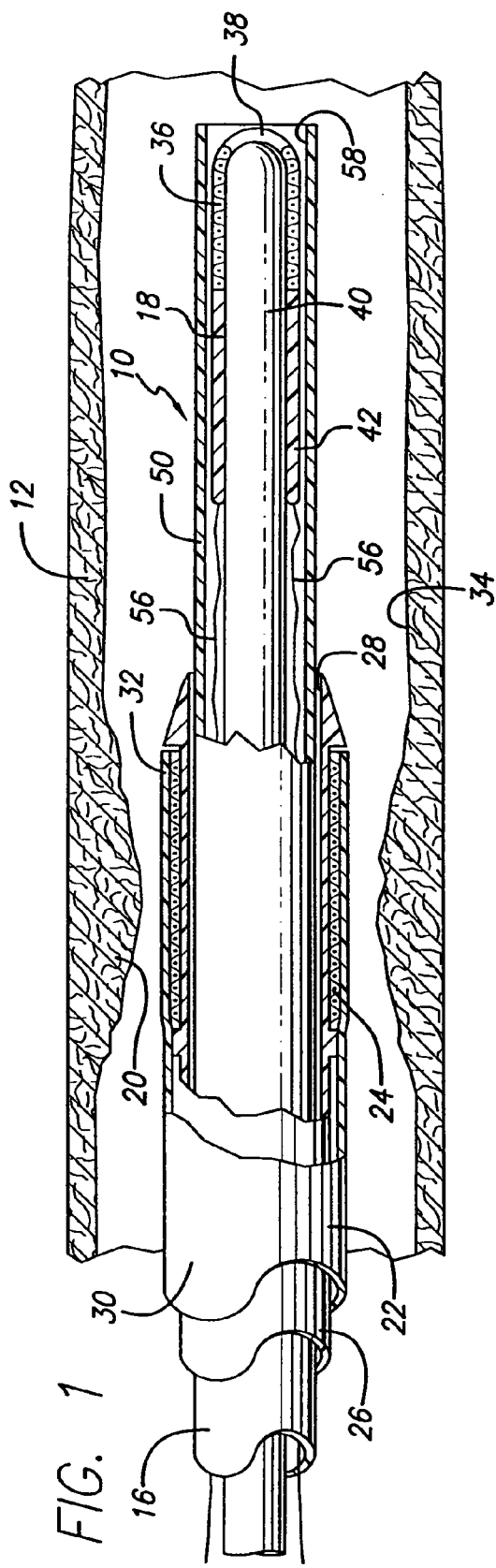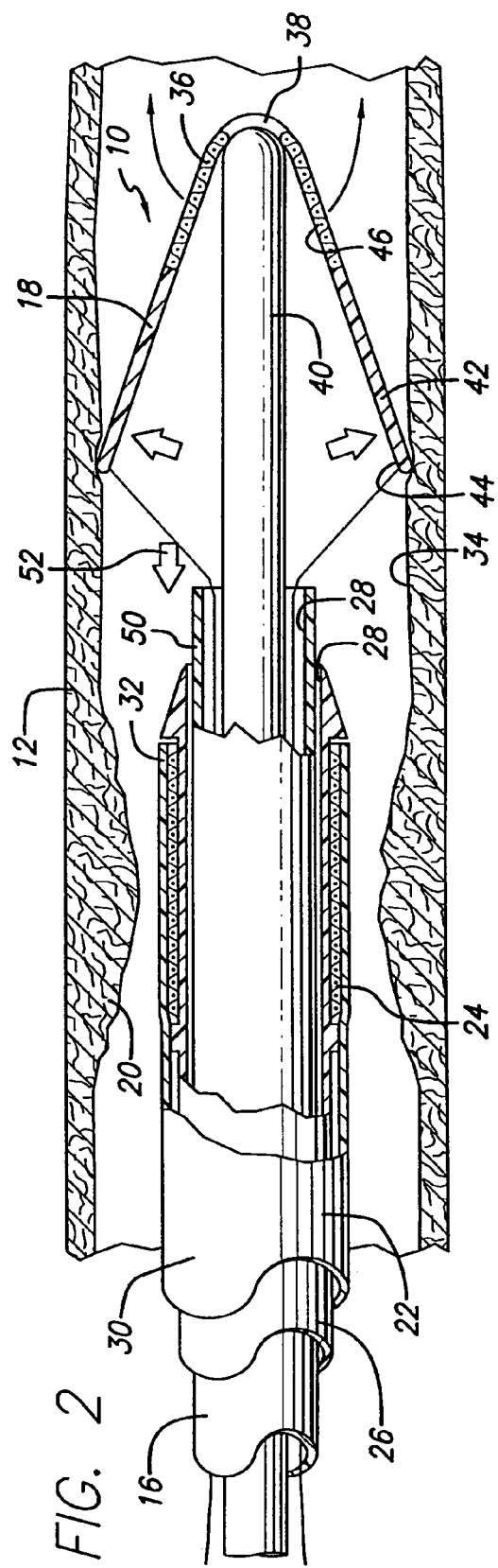

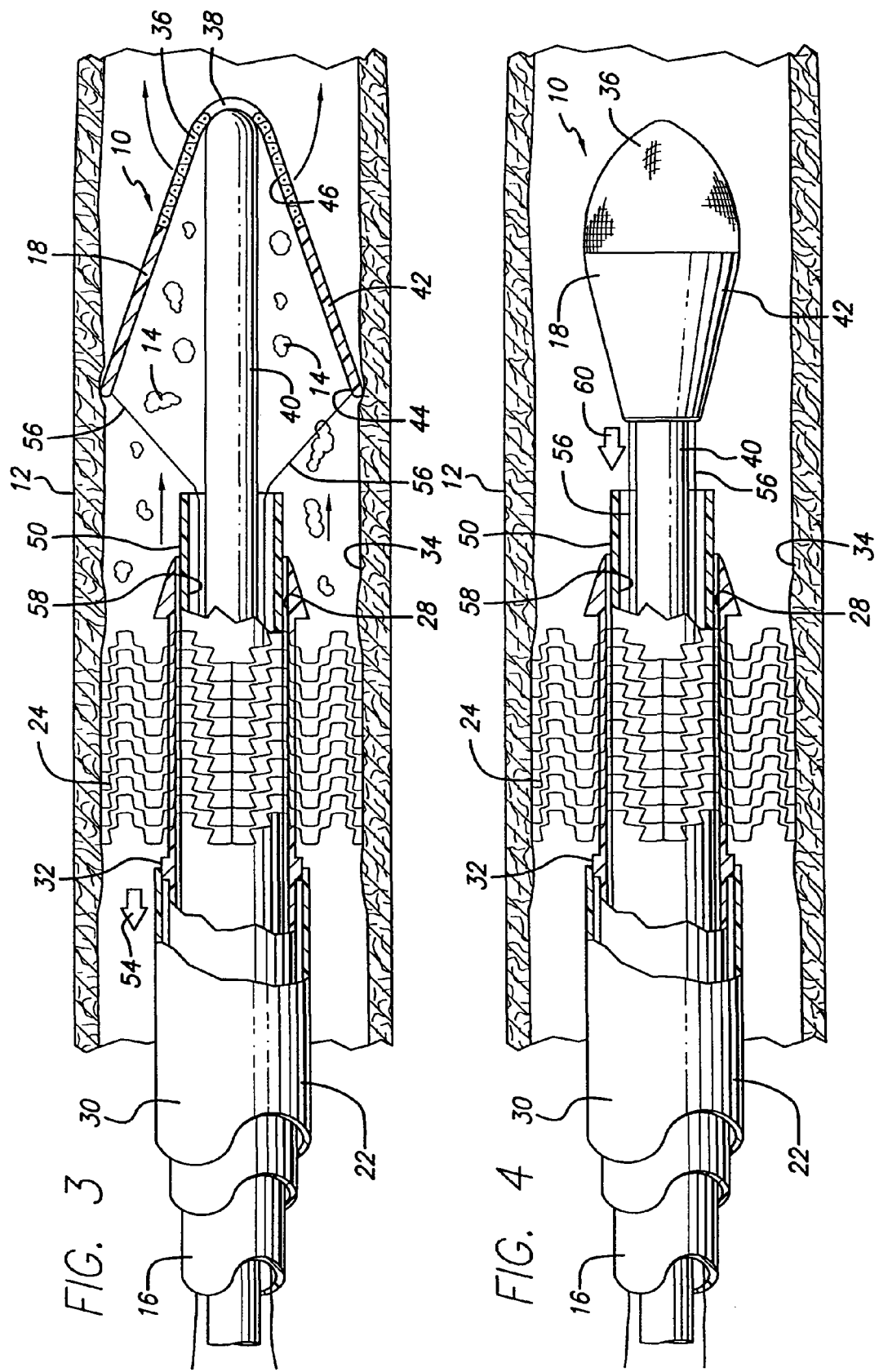

DEVICE FOR, AND METHOD OF, BLOCKING EMBOLI IN VESSELS SUCH AS BLOOD ARTERIES

CROSS-REFERENCE TO RELATED APPLICATIONS

This application is a continuation of U.S. Ser. No. 09/476,689, filed Dec. 30, 1999. The contents of which are hereby incorporated by reference.

BACKGROUND OF THE INVENTION

This invention relates to a device for, and methods of, preventing emboli from a lesion in a vessel from passing through the vessel. The device and method of the present invention are especially adapted to be used in preventing emboli in blood from passing through a vessel such as an artery.

In recent years, numerous procedures have been adapted for expanding blood vessels (e.g. arteries), at the positions of lesions in the blood vessels, so that blood can flow through the blood vessels without obstruction from the lesions. In the process of expanding such blood vessels at the positions of the lesions, emboli may become detached from the lesions and enter the bloodstream and subsequently migrate through the patient's vasculature to cut off or reduce the amount of oxygenated blood being supplied to sensitive organs such as the brain, which may induce trauma.

Procedures have also been adapted in recent years for preventing embolic debris from flowing through the vessels in the direction of the blood flow. For example, filters have been provided for trapping the emboli. When lesions develop in the carotid artery of a patient, the placement of a filter in the patient's vasculature can somewhat reduce the movement of emboli to blood vessels leading to the patient's brain, thereby preventing strokes from occurring.

Such filters are usually delivered in a collapsed position through the patient's vasculature and are then expanded once in place in the patient's blood vessel to trap the emboli. After emboli have been trapped, the filter is collapsed and removed (with the trapped emboli) from the vessel. Unfortunately, it is possible for some of the trapped emboli to escape from the filter during the time that the filter is being collapsed and/or removed from the blood vessel. When an interventional procedure is being performed in a carotid artery, even a trace release of emboli can be damaging. For these reasons, attempts to treat lesions in the carotid arteries have been somewhat limited due to the danger presented if all of the embolic debris is not collected during the procedure.

Therefore, in light of the above, it would be desirable for a device and method which can be utilized to treat an occluded vessel and trap any emboli that may be formed during the vascular procedure. Such a device and method must also prevent the emboli from escaping from the filter during the time that the filter is being collapsed and/or removed from the blood vessel (e.g. the carotid arteries). Although considerable progress has been made in recent years in providing a satisfactory filter, it would still be desirable to provide a filter which is simple, cost efficient and trustworthy in construction, and is easy to deploy and remove from the patient's vasculature with little or no adverse impact or immulogical response to the patient.

SUMMARY OF THE INVENTION

The present invention is directed to a filtering device for trapping and removing emboli from a body vessel (e.g. an artery). In one embodiment, the filtering device includes a catheter portion and a filtering portion disposable in the vessel at a position downstream from a lesion formed within the vessel. The filtering device includes a filtering member made from a resilient material having properties of passing fluid (e.g. blood) while blocking the passage of emboli in the fluid. This material may be selected from a group consisting of blood filter material and a braided/woven biocompatible material with the properties specified above. The inner end of the filtering member is attached to an inner shaft which provides for the disposition of the filtering portion of the device in the vessel at the position past the lesion and for the withdrawal of the filtering portion as well.

A directional member, attached to the filtering member, has a length extending at least to the vessel wall. This directional member can be made from a pliable and elongatable material with properties of blocking fluid and emboli passage. The directional member is disposed to direct the fluid and any emboli in the fluid into the filtering member. The filtering and directional members generally are disposed at an acute angle relative to the shaft. The directional member is designed to create a deep pocket which is used to trap the emboli while allowing the fluid to pass there through to downstream vessels. In one particular embodiment, the directional member has a conical shape which acts much like a parachute when deployed in the fluid flow. The directional member opens up when subjected to the fluid flow and remains in a fully deployed position to partially occlude the vessel, due to fluid build proximal to the directional member. The filtering member located within the deep pocket formed by the directional member provides the filtering media for trapping the emboli. In this fashion, the directional member is designed to channel all fluid and emboli into the deep pocket to allow the filtering member to perform the necessary filtration. The design of the deep pocket helps to retain the emboli deep within the filtering device, sufficiently past the inlet opening of the directional member. As a result, there is a less possibility that trapped emboli will "backflow" into the artery as the filtering portion of the device is being collapsed and removed from the patient's vasculature.

An interventional device, such as an expandable member (e.g., a balloon catheter) and a stent, can be disposed in the vessel to treat the lesion and open the vessel at the lesion position. Any suitable interventional device can be used with the present invention. After the interventional device has performed the procedure, it is collapsed and removed from the vessel. Emboli created during the interventional procedure are released into the fluid flow (e.g. bloodstream) and are trapped within the deep pocket formed by the directional member and filtering member.

In one aspect of the invention, the catheter portion of the filtering device includes an outer sheath or sleeve which extends co-axially over the filtering portion of the device. The filtering portion can be deployed from the confides of the sheath by simply moving the inner shaft of the catheter portion in an outward direction from the sheath, or by retracting the sheath, or a combination of both. Once the inlet opening of the directional member is deployed in the fluid flow, it will expand outwardly (like a deployed parachute) within the vessel. Restraining wires, attached to the directional member near its inlet opening extend along the catheter portion to a location outside the patient. When the device is to be collapsed and removed from the patient, the physician simply retracts these wires to collapse the directional member and draw at least a portion of the directional member (including the inlet opening) back into the lumen of the outer sheath. This helps prevent backflow of trapped emboli into the vessel.

Any trapped emboli which is capable of backflowing from the filtering portion will now be trapped within the inner lumen of the sheath and will not be discharged into the vessel. Thereafter, the entire device can be removed from the patient with little risk of losing any trapped emboli.

These and other advantages of the present invention will become more apparent from the following detailed description of the invention, when taken in conjunction with the accompanying exemplary drawings.

BRIEF DESCRIPTION OF THE DRAWINGS

FIG. 1 is an elevational view, primarily in section, of a preferred embodiment of device for trapping and removing emboli produced in a vessel during an interventional procedure, along with an interventional device which includes a stent delivery catheter and a self-expanding stent.

FIG. 2 is an enlarged fragmentary elevational view, primarily in section, of the preferred embodiment of FIG. 1 showing in additional detail the filtering device in an expanded position against the wall of the vessel.

FIG. 3 is an enlarged fragmentary elevational view, primarily in section, of the filtering device in the expanded position and additionally shows the stent deployed against the wall of the vessel in the area of treatment which results in the creation of emboli that are released into the fluid flow of the vessel.

FIG. 4 is an enlarged fragmentary elevational view, primarily in section, of the filtering device in the collapsed position with trapped emboli contained therein after the expansion of the stent against the wall.

DETAILED DESCRIPTION OF THE PREFERRED EMBODIMENTS

Figure 5:
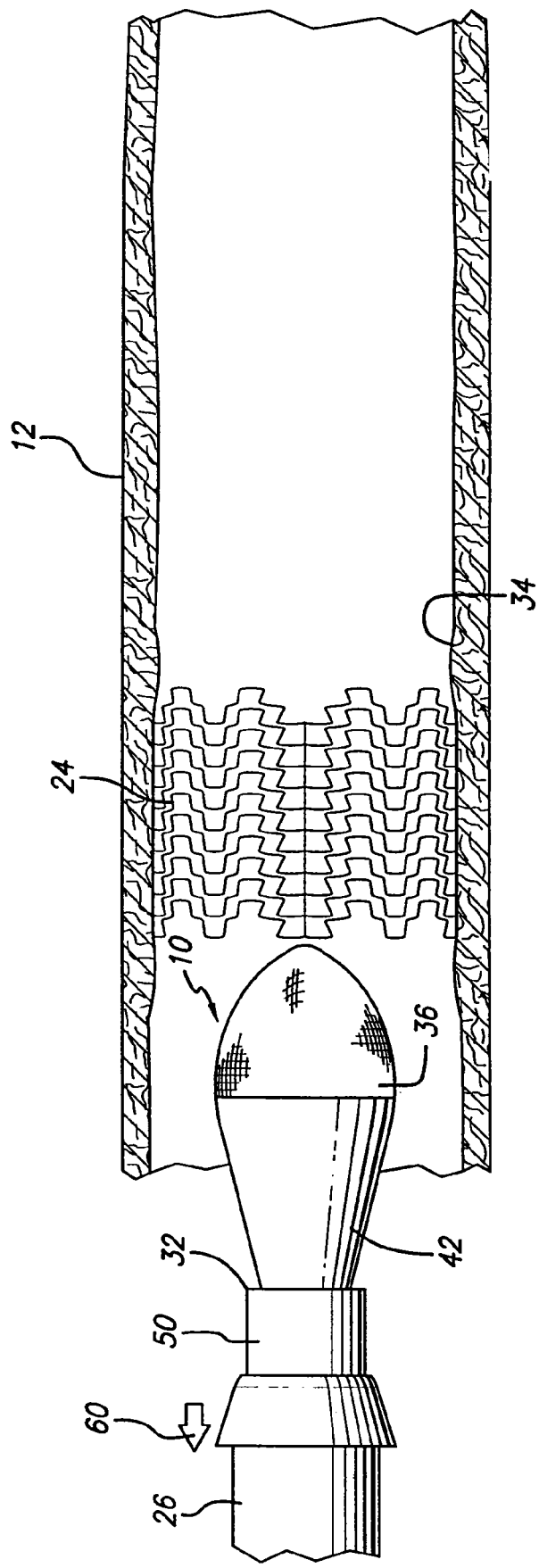
FIG. 5 is an enlarged fragmentary elevational view, primarily in section, showing the filtering device being withdrawn from the vessel.

A first preferred embodiment of a filtering device made in accordance with the present invention, generally indicated at 10, is shown in FIGS. 1-5 of the drawings. The filtering device 10 is adapted to be disposed in a blood vessel 12 to pass the blood in the vessel and block the passage of emboli 14 (FIG. 3) in the blood. The filtering device 10 includes a catheter portion 16 which is designed to deploy a filtering portion 18 in the vessel 12 to trap and remove emboli 14 from the vessel. The emboli 14 are produced when the vessel 12 is treated at the position of a lesion 20 during an intervention procedure such as, a balloon angioplasty procedure, a stenting procedure, an atherectomy procedure and the like. The present invention is designed to collect and remove such embolic debris from the artery to prevent the blockage of the smaller vessels downstream from the area of treatment. The system 10 is especially adapted to prevent blockage of small blood vessels leading to the brain which, if blocked, can result in the patient suffering a stroke.

An interventional device, such as a stent delivery catheter 22 and a self-expanding stent 24, can be utilized to treat the lesion 20 and open up the artery 12 to increase blood flow therethrough. This stent delivery catheter 22 and the stent 24 may be constructed in a manner well known in the art. The delivery catheter 22 and the stent 24 may be disposed at the position of the lesion 20 as shown schematically in FIG. 1. The delivery catheter 22 includes an inner tubular member 26 onto which the compressed or collapsed stent 24 is mounted. This inner tubular member 26 includes an inner lumen 28 which allows the stent delivery catheter 22 to be disposed over the catheter portion 16 of the device 10 in a co-axial arrangement. This allows the stent delivery catheter 22 to be delivered to the area of treatment using over-the-wire techniques. The stent delivery catheter 22 includes an outer restraining sheath 30 which extends over the inner tubular member 26 in a co-axial arrangement and is used to restrain the collapsed stent 24 until it is ready to be deployed. Both the outer retraining sheath 30 and inner tubular member 26 have proximal ends (not shown) which extent outside of the patient. In use, the physician moves the proximal ends to retract the distal end 32 of the restraining sheath 30 the necessary distance to expose and deploy the self-expanding stent 24. Once the stent 24 is positioned across the lesion 20, the restraining sheath 30 can be retracted to expose the stent 24 and allow it to self expand against the wall 34 of the vessel 12. The opening in the vessel 12 is maintained by the stent 24 even after the delivery catheter 22 is withdrawn from the vessel.

The filtering portion 18 of the device 10 is constructed to be inserted into the vessel 12 at a position past the lesion 20 in the direction of the fluid flow (i.e. downstream from the lesion). The filtering portion 18 includes a filtering member 36 disposed at the interior of the vessel 12. The filtering member 36 may be made from a material having properties of passing the fluid such as blood and of blocking the passage of the emboli 14 in the blood. For example, the material for the member 12 may be selected from a group consisting of blood filter material and a braided/woven biocompatible material. Commercially available materials such as Gortex also can be used. The filter can be made from polymeric or nylon material which has openings of a desired sized formed therein to allow fluid to pass but to capture emboli of a desired size. The distal end 38 of the filtering member 36 is attached to an inner shaft 40 which provides for the disposition of the filtering portion 18 in the vessel 12 at the position past the lesion 20. The shaft 40 may include an inner lumen (not shown) which allows the catheter portion 16 to be delivered into the patient's vasculature over a guidewire (not shown) using over the wire techniques. A directional member 42 is attached to the filtering member 36, preferably at the outer periphery of the filtering member 36. The directional member 42 may be made from a material having properties of blocking the passage of the fluid such as blood and the emboli in the blood. The directional member 42 is preferably highly pliable and/or highly elongatable. This provides for the inlet opening 44 of the directional member 42 to be disposed tightly against the wall 34 defining the vessel 12, thereby preventing fluid and emboli from leaking along the wall 34. The directional member can have a cone or cone-shape like construction, although the directional member can take on other shapes as well. The directional member 42 is disposed relative to the filtering member 36 to direct the fluid and emboli in the vessel 12 to the filtering member 36. The filtering member 36 and directional member 42 form an acute angle with the shaft 40 and the wall 34 of the vessel 12 to create a deep pocket 46 which is used to trap the emboli while allowing the fluid to pass there through to downstream vessels. The directional member 42 opens up when subjected to the fluid flow and remains in a fully deployed position to partially occlude the vessel, due to fluid build proximal to the directional member. The filtering member 36 located within this deep pocket 46 provides the filtering media for trapping the emboli. In this fashion, the directional member is designed to channel all fluid and emboli into the deep pocket 46 to allow the filtering member to perform the necessary filtration. The design of the deep pocket 46 helps to retain the emboli deep within the filtering device, sufficiently past the inlet opening 44 of the directional member 42. As a result, there is a less possibility that trapped emboli will "backflow" into the vessel as the filtering portion 18 of the device 10 is being collapsed and removed from the patient's vasculature.

The filtering device 10 is used during vascular intervention, in particular preferably during carotid artery angioplasty and stenting. The filtering device 10 is advanced in the artery so that the stent 24 is disposed at the lesion 20 with the filtering portion 18 disposed past the lesion 20 in the direction of the fluid flow. During the delivery of the filtering portion 18 to the position past the lesion 20, the filtering portion 18 may be housed within a sheath 50, which forms a part of the catheter portion 16 of the device 10, so as to have a constricted (or contracted) relationship. The sheath 50 is then moved in a direction away from the filtering portion 18 as indicated by arrow 52 in FIG. 2. This causes the directional member 42 to expand outwardly so that the member engages the wall 34 of the vessel 12. The stent 24 is then expanded against the wall 34 of the vessel 12 to open the artery at the position of the lesion 20. Any emboli 14 produced as a result of the expansion of the stent 24 against the lesion 20 flow to the filtering portion 18. The directional member 42 directs the fluid and emboli 14 to the filtering member 36 which passes the fluid but captures the emboli 14.

When emboli 14 have been trapped by the filter, the stent delivery catheter 22 is withdrawn in the vessel 12. Any emboli 14 produced by the withdrawal of the stent delivery catheter will likewise be trapped by the filtering portion 18. The withdrawal of the stent delivery catheter 22 is indicated by a hollow arrow 54 in FIG. 3. The filtering device 10 includes restraining wires 56, attached to the directional member 42 near its inlet opening 44, which extend along the catheter portion 16 to a location outside the patient. When the filtering portion 18 is to be collapsed and removed from the patient, the physician simply retracts these restraining wires 56 to collapse the directional member 42 and draw at least a portion of the directional member (including the inlet opening 44) back into the lumen 58 of the outer sheath 50. This helps prevent backflow of trapped emboli into the vessel. Any trapped emboli which is capable of bacflowing from the filtering portion will now be trapped within the inner lumen 58 of the sheath 50 and will not be discharged back into the vessel 12. Thereafter, the entire device 10 can be removed from the patient with little risk of losing any trapped emboli 14. The removal of the device 10 from the vessel 12 is indicated by hollow arrows 60 in FIGS. 4 and 5. While only two restraining wires are shown in the figures, any number of wires can be utilized to help collapse the directional member 42 and retract it back into the inner lumen 58 of the sheath 50. Other means for collapsing the directional member 42 also can be used without departing from the spirit and scope of the present invention.

The catheter portion 16 of the filtering device 10 made be made from suitable polymeric materials well known in the art. The restraining wires can be made from suitable metals or polymeric materials which have sufficient axial strength so as not to break when being retracted to collapse the directional member. The device 10 can be used in conjunction with current compatible devices such as balloon catheters, stent delivery systems, guide wires, guiding catheters and angiographic catheters.

Although this invention has been disclosed and illustrated with reference to particular embodiments, the principles involved are susceptible for use in numerous other embodiments which will be apparent to persons of ordinary skill in the art. The invention is, therefore, to be limited only as indicated by the scope of the appended claims.

What is claimed:

1. A filtering device for blocking the passage of emboli through a body vessel, comprising:
   a directional member made from a pliable, fluid impermeable material, the directional member being movable from a collapsed position to an expanded, deployed position by the fluid flow in the body vessel, the directional member having a truncated conical shape which includes an inlet opening for receiving fluid flow therethrough and an outlet opening through which fluid passes through;
   a filtering member made from a material which blocks passage of emboli entrained in the fluid by allows passage of the fluid therethrough, the filtering member being attached to the directional member so that fluid directed into the directional member passes through the filtering member;
   an elongate tubular member having an internal lumen and a distal section and proximal section, the elongate tubular member having an outer diameter sized to allow an interventional device to be advanced over it to position an interventional device within the body vessel, wherein the directional member and filtering member are maintained in the collapsed position within the internal lumen of distal section of the tubular member, the proximal section of the elongate member being located outside of the body vessel when the directional member and filtering member are placed within the body vessel;
   a shaft member having a distal end and a proximal end, the shaft member being slidably disposed within the lumen of the elongate tubular member for moving the directional and filtering member out of the lumen of the elongate tubing tubular member for deployment by the fluid flow in the body vessel, the shaft member being movable from a location outside the body vessel to move the directional member and filtering member from the collapsed position; and
   a restraining wire attached to the directional member which extends along the length of the elongate tubular member, the restraining wire being retractable from a location outside the body vessel to move the directional member and filtering member back to the collapsed position.

2. The filtering device of claim 1, wherein:
   the directional member is elongated and adapted to be disposed against the wall of the body vessel when placed in the expanded, deployed position.

3. The filtering device of claim 1 wherein:
   the directional member directs body fluid into the filtering member.

4. The filtering device of claim 1, wherein:
   the filtering member has an inlet opening and the restraining wire is adapted to draw at least the inlet opening of the filtering member into a recovery sheath.

5. The filtering device of claim 1, wherein:
   the restraining wire extends within the lumen of the elongate tubular member.

6. The filtering device of claim 1, wherein:
   the shaft member contacts the interior of the filtering member to move the filtering member and directional member out of the lumen of the elongate tubular member.

7. The filtering device of claim 1, wherein:
   the restraining wire extends outwardly from the lumen when the filter is deployed.

8. A method of filtering emboli entrained in the body fluid in a body vessel, comprising:

providing a filtering device having a directional member made from a pliable, fluid impermeable material, the directional member being movable from a collapsed position to an expanded, deployed position by the fluid flow in the body vessel, the directional member having a truncated conical shape which includes an inlet opening for receiving fluid flow therethrough and an outlet opening through which fluid passes through; a filtering member made from a material which blocks passage of emboli entrained in the fluid by allows passage of the fluid therethrough, the filtering member being attached to the directional member so that fluid directed into the directional member passes through the filtering member; an elongate tubular member having an internal lumen and a distal section and proximal section, the elongate tubular member having an outer diameter sized to allow an interventional device to be advanced over it to position an interventional device within the body vessel, wherein the directional member and filtering member are maintained in the collapsed position within the internal lumen of distal section of the tubular member, the proximal section of the elongate member being located outside of the body vessel when the directional member and filtering member are placed within the body vessel; a shaft member having a distal end and a proximal end, the shaft member being slidably disposed within the lumen of the elongate tubular member for moving the directional and filtering member out of the lumen of the elongate tubing for deployment by the fluid flow in the body vessel, the shaft member being movable from a location outside the body vessel to move the directional member and filtering member from the collapsed position; and a restraining wire attached to the directional member which extends along the length of the elongate tubular member, the restraining wire being retractable from a location outside the body vessel to move the directional member and filtering member back to the collapsed position;

placing the directional member and filtering member into the lumen of the distal section of the elongate tubular member;

advancing the filtering device into a desired body vessel;

manipulating the shaft member to allow the directional member and filtering member to exit the lumen of the elongate tubular member;

allowing fluid flow in the body vessel to expand the directional member into its expanded, deployed position;

advancing interventional device over the elongate tubular member to a desired location in the body vessel;

performing an interventional procedure in the body vessel;

capturing emboli entrained in the body fluid in the filtering member;

removing the interventional device from the body lumen;

retracting the proximal end of the restraining wire to pull at least a portion of the directional member into the lumen of the elongate tubular member; and removing the filtering device from the body vessel.

\* \* \* \* \*